(12) United States Patent
Iwamori et al.

(10) Patent No.: US 12,353,990 B2
(45) Date of Patent: Jul. 8, 2025

(54) TIME-WINDOW BASED ATTENTION LONG SHORT-TERM MEMORY NETWORK OF DEEP LEARNING

(71) Applicant: International Business Machines Corporation, Armonk, NY (US)

(72) Inventors: Toshiya Iwamori, Tokyo (JP); Akira Koseki, Yokohama (JP); Hiroki Yanagisawa, Tokyo (JP); Takayuki Katsuki, Tokyo (JP)

(73) Assignee: International Business Machines Corporation, Armonk, NY (US)

( * ) Notice: Subject to any disclaimer, the term of this patent is extended or adjusted under 35 U.S.C. 154(b) by 890 days.

(21) Appl. No.: 16/926,741

(22) Filed: Jul. 12, 2020

(65) Prior Publication Data

US 2022/0013239 A1 Jan. 13, 2022

(51) Int. Cl.
*G06N 3/08* (2023.01)
*G16H 50/30* (2018.01)
*G16H 50/50* (2018.01)
*G16H 50/70* (2018.01)
*G16H 70/60* (2018.01)

(52) U.S. Cl.
CPC .............. *G06N 3/08* (2013.01); *G16H 50/30* (2018.01); *G16H 50/50* (2018.01); *G16H 50/70* (2018.01); *G16H 70/60* (2018.01)

(58) Field of Classification Search
CPC .......... G06N 3/08; G16H 50/50; G16H 50/30; G16H 50/70; G16H 70/60
See application file for complete search history.

(56) References Cited

U.S. PATENT DOCUMENTS

2018/0336452 A1\* 11/2018 Tschernezki .......... G06N 3/044
2019/0034589 A1 1/2019 Chen
(Continued)

FOREIGN PATENT DOCUMENTS

CN 110289096 A 9/2019
CN 110767279 A 2/2020

OTHER PUBLICATIONS

"Exploring Interpretable LSTM Neural Networks over Multi-Variable Data," arXiv, Proceedings of the 36th International Conference on Machine Learning, Long Beach, California, PMLR 97 (Year: 2020).\*
(Continued)

*Primary Examiner* — Michael J Huntley
*Assistant Examiner* — Paul J Breene
(74) *Attorney, Agent, or Firm* — Yee & Associates, P.C.

(57) ABSTRACT

A computer-implemented method, a computer program product, and a computer system for using a time-window based attention long short-term memory (TW-LSTM) network to analyze sequential data with time irregularity. A computer splits elapsed time into a predetermined number of time windows. The computer calculates average values of previous cell states in respective ones of the time windows and sets the average values as aggregated cell states for the respective ones of the time windows. The computer generates attention weights for the respective ones of the time windows. The computer calculates a new previous cell state, based on the aggregated cell states and the attention weights for the respective ones of the time windows. The computer updates a current cell state, based on the new previous cell state.

18 Claims, 11 Drawing Sheets

(56) References Cited

U.S. PATENT DOCUMENTS

2019/0180882 A1    6/2019  Han
2020/0192970 A1*  6/2020  Ma ........................ G06F 17/16

OTHER PUBLICATIONS

"ATTAIN: Attention-based Time-Aware LSTM Networks for Disease Progression Modeling," Proceedings of the Twenty-Eighth International Joint Conference on Artificial Intelligence (IJCAI-19) (Year: 2019).*
"Exploring Interpretable LSTM Neural Networks over Multi-Variable Data," arXiv, Proceedings of the 36th International Conference on Machine Learning, Long Beach, California, PMLR 97 (Year: 2020) (Year: 2020).*
"Understanding LSTM Networks," Colah's Blog, Christopher Olah (Year: 2015).*
"Average Definition and Meaning," Merriam-Webster (Year: 2025).*
"RETAIN: An Interpretable Predictive Model for Healthcare using Reverse Time Attention Mechanism," NIPS'16: Proceedings of the 30th International Conference on Neural Information Processing Systems (Year: 2016).*
"Speech Emotion Classification Using Attention-Based LSTM," IEEE/ACM Transactions on Audio, Speech, and Language Processing (Year: 2019).*
Bai, et al., "Interpretable Representation Learning for Healthcare via Capturing Disease Progression through Time", KDD 2018, ACM, Aug. 2018, pp. 43-51.
Baytas, et al., "Patient Subtyping via Time-Aware LSTM Networks", KDD'17, ACM, Aug. 2017, pp. 65-74.
Chang et al., "Uric Acid in the Follow-Up Determines 30% Decline in Estimated GFR Over 2 Years: a Propensity Score Analysis", Kidney Blood Press Res., 42(6), 2017, pp. 1053-1067.
Che et al., "An RNN Architecture with Dynamic Temporal Matching for Personalized Predictions of Parkinson's Disease", Proceedings of the 2017 SIAM International Conference on Data Mining, 2017, pp. 198-206.
Cheng et al., "Risk Prediction with Electronic Health Records: A Deep Learning Approach", Proceedings of the 2016 SIAM International Conference on Data Mining, 2016, pp. 432-440.
Choi et al., "Doctor AI: Predicting Clinical Events via Recurrent Neural Networks", arXiv:1511.05942v11 [cs.LG], Sep. 28, 2016, 18 pages.
Choi et al., "GRAM: Graph-based Attention Model for Healthcare Representation Learning", In KDD'17, ACM, Aug. 2017, pp. 787-795.
Choi et al., "MiME: Multilevel Medical Embedding of Electronic Health Records for Predictive Healthcare", 32nd Conference on Neural Information Processing Systems (NIPS 2018), 2018, 17 pages.
Choi, et al., "RETAIN: An Interpretable Predictive Model for Healthcare using Reverse Time Attention Mechanism", 29th Conference on Neural Information Processing Systems (NIPS 2016), 2016, 13 pages.
Esteban et al., "Predicting Clinical Events by Combining Static and Dynamic Information using Recurrent Neural Networks", 2016 IEEE International Conference on Healthcare Informatics, 2016, pp. 93-101.
Hochreiter, et al., "Long Short-Term Memory", Neural Computation, 9(8), 1997, pp. 1735-1780.
Kartoun, "A Methodology to Generate Virtual Patient Repositories", arXiv 1608.00570, 2016, 10 pages.
Levey et al., "A New Equation to Estimate Glomerular Filtration Rate", Annals of Internal Medicine, 2009, pp. 604-612.
Lipton et al., "Learning to Diagnose with LSTM Recurrent Neural Networks", arXiv:1511.03677v3 [cs.LG], Nov. 17, 2015, 14 pages.
Liu et al., "Learning the Joint Representation of Heterogeneous Temporal Events for Clinical Endpoint Prediction", The Thirty-Second AAAI Conference on Artificial Intelligence (AAAI-18), 2018, pp. 109-116.
Ma et al., "Dipole: Diagnosis Prediction in Healthcare via Attention-based Bidirectional Recurrent Neural Networks", In KDD'17, ACM, 2017, pp. 1903-1911.
Ma et al., "Health-ATM: A Deep Architecture for Multifaceted Patient Health Record Representation and Risk Prediction", In SDM, SIAM, 2018, pp. 261-269.
Makino, et al., "Artificial Intelligence Predicts the Progression of Diabetic Kidney Disease Using Big Data Machine Learning", Scientific Reports, 9(1):11862, 2019, 9 pages.
Mell, et al., "The NIST Definition of Cloud Computing", National Institute of Standards and Technology, Special Publication 800-145, Sep. 2011, 7 pages.
Pham et al., "DeepCare: A Deep Dynamic Memory Model for Predictive Medicine", arXiv:1602.00357v2 [stat.ML], Apr. 10, 2017, 27 pages.
Zhang, et al., "ATTAIN: Attention-based Time-Aware LSTM Networks for Disease Progression Modeling", Proceedings of the Twenty-Eighth International Joint Conference on Artificial Intelligence (IJCAI-19), 2019, pp. 4369-4375.

* cited by examiner

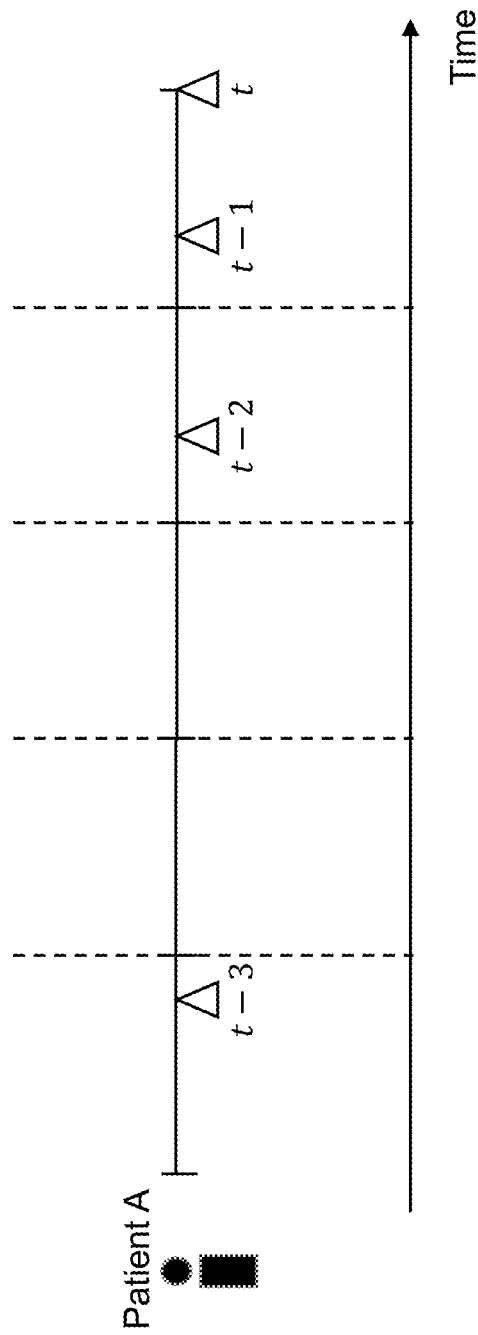
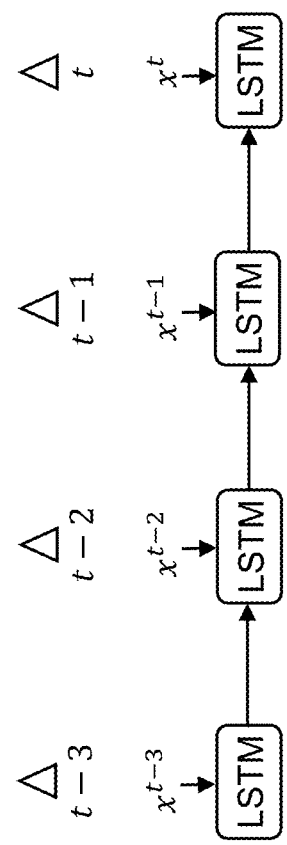
FIG. 1(A)
FIG. 1(B)

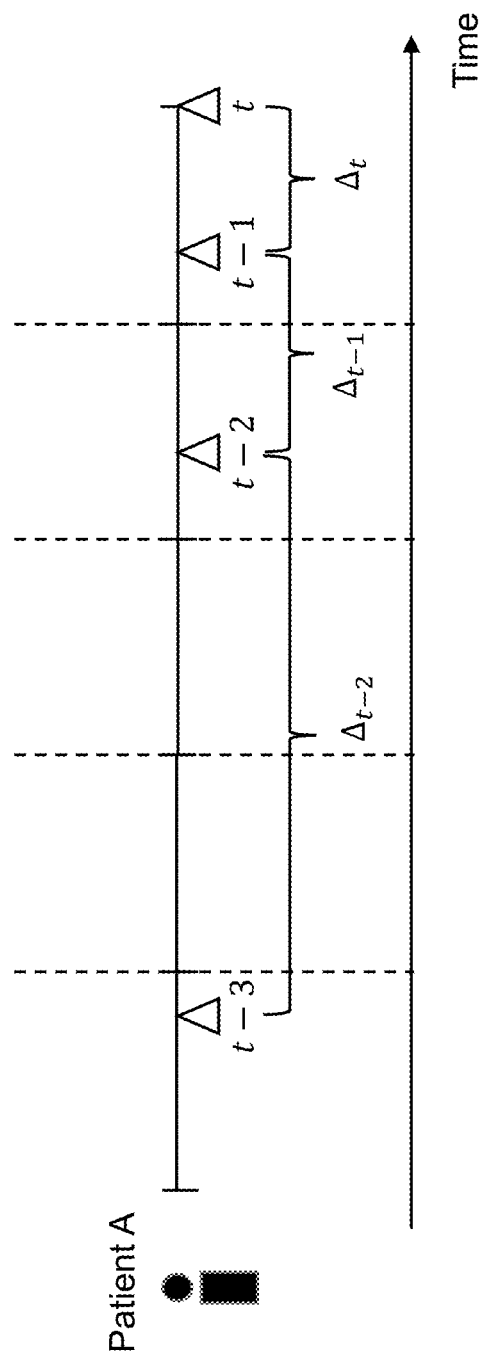
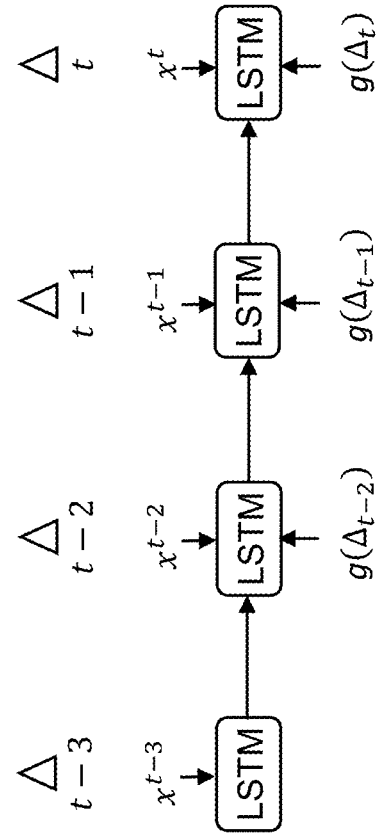
FIG. 2(A)
FIG. 2(B)

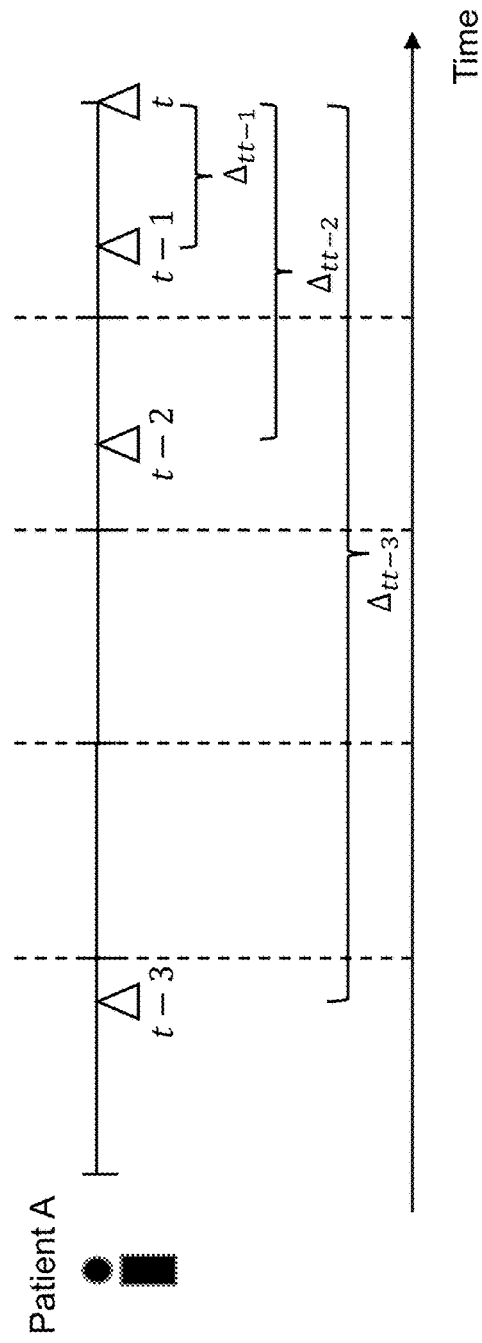
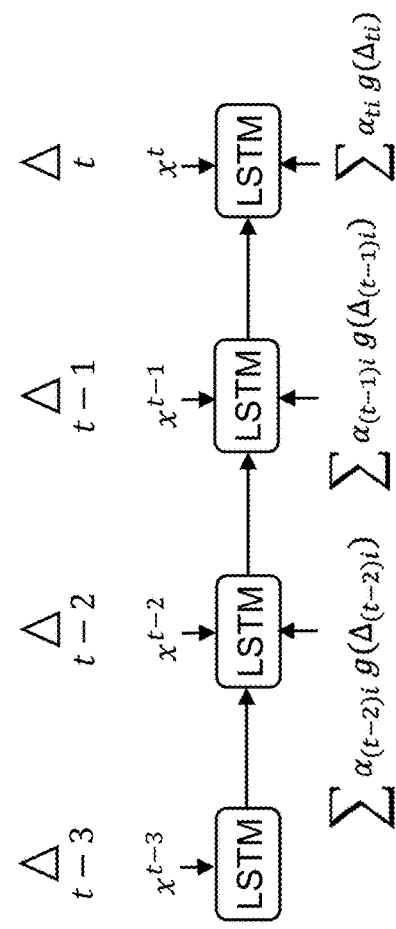
FIG. 3(A)
FIG. 3(B)

TIME-WINDOW BASED ATTENTION LONG SHORT-TERM MEMORY NETWORK OF DEEP LEARNING

BACKGROUND

The present invention relates generally to an artificial recurrent neural network (RNN) architecture of deep learning, and more particularly to using a time-window based attention long short-term memory (TW-LSTM) network to analyze sequential data with time irregularity.

Analyzing electronic health records (EHR) is essential to make clinical treatments in the early stage of a disease and prevent its progression. Each EHR record represents a patient's history as a sequence of information including vital signs, lab results, and medications. Deep neural networks (DNN) have shown promising results in disease progression modeling and risk prediction with EHR. In particular, recurrent neural networks (RNN) are useful for learning patterns from such sequential data. Long short-term memory (LSTM) is a variant of RNN that captures long-term dependencies which often occur in EHR.

The challenge to applying LSTM to EHR data is the time irregularity of EHR data. In EHR data, the time interval between visits such as lab results and medications varies from one patient to another, depending on each patient's health. This problem is called a time interval lag. Additionally, when the time interval lags become too large, the relationship between the time step and the actual elapsed time to current visit depends on each patient, where the time step means the number of observations. This problem is called a time step lag.

LSTM cannot handle the time interval lag and the time step lag. In using LSTM, it is assumed that the time intervals between cell states in a sequence are constant and that the relationship between the actual elapsed time and each time step is invariant from one record to the another record.

To address the time interval lag in EHR, previous approaches incorporate the elapsed time into their models. In time-aware long short-term memory (T-LSTM), the previous cell state is adjusted (discounted) based on the elapsed time when the current cell state is updated. Attention-based time-aware disease progression model (ATTAIN), which is an extension of the architecture of T-LSTM, uses not only one previous cell state but also a number of previous cell states for updating the current cell state, while it adjusts the weights for the previous cell states. ATTAIN improves interpretability as well as prediction performance by using a time decay function and an attention mechanism. However, these approaches cannot handle the relationship between the actual elapsed time and the time step that depends on each patient. The time step lag is not adjusted in these methods. Furthermore, the time step lag is critical for understanding attention. Attention is a method that helps to interpret the outputs of a DNN as well as LSTM. When the relationship between elapsed times and time steps occur, it may become hard to interpret the estimated attention. The general attention mechanism cannot capture such time variations with fluctuating observation intervals.

SUMMARY

In one aspect, a computer-implemented method for using a time-window based attention long short-term memory (TW-LSTM) network to analyze sequential data with time irregularity is provided. The computer-implemented method comprises splitting elapsed time into a predetermined number of time windows. The computer-implemented method further comprises calculating average values of previous cell states in respective ones of the time windows and setting the average values as aggregated cell states for the respective ones of the time windows. The computer-implemented method further comprises generating attention weights for the respective ones of the time windows. The computer-implemented method further comprises calculating a new previous cell state, based on the aggregated cell states and the attention weights for the respective ones of the time windows. The computer-implemented method further comprises updating a current cell state, based on the new previous cell state.

In another aspect, a computer program product for using a time-window based attention long short-term memory (TW-LSTM) network to analyze sequential data with time irregularity is provided. The computer program product comprises a computer readable storage medium having program instructions embodied therewith, and the program instructions are executable by one or more processors. The program instructions are executable to: split elapsed time into a predetermined number of time windows; calculate average values of previous cell states in respective ones of the time windows; set the average values as aggregated cell states for the respective ones of the time windows; generate attention weights for the respective ones of the time windows; calculate a new previous cell state, based on the aggregated cell states and the attention weights for the respective ones of the time windows; and update a current cell state, based on the new previous cell state.

In yet another aspect, a computer system for using a time-window based attention long short-term memory (TW-LSTM) network to analyze sequential data with time irregularity is provided. The computer system comprises one or more processors, one or more computer readable tangible storage devices, and program instructions stored on at least one of the one or more computer readable tangible storage devices for execution by at least one of the one or more processors. The program instructions are executable to split elapsed time into a predetermined number of time windows. The program instructions are further executable to calculate average values of previous cell states in respective ones of the time windows. The program instructions are further executable to set the average values as aggregated cell states for the respective ones of the time windows. The program instructions are further executable to generate attention weights for the respective ones of the time windows. The program instructions are further executable to calculate a new previous cell state, based on the aggregated cell states and the attention weights for the respective ones of the time windows. The program instructions are further executable to update a current cell state, based on the new previous cell state.

BRIEF DESCRIPTION OF THE SEVERAL VIEWS OF THE DRAWINGS

FIG. 1(A) and FIG. 1(B) illustrate a long short-term memory (LSTM) model used for analyzing electronic health records (EHR).

FIG. 2(A) and FIG. 2(B) illustrate a time-aware long short-term memory (T-LSTM) model used for analyzing electronic health records (EHR).

FIG. 3(A) and FIG. 3(B) illustrate an attention-based time-aware disease progression (ATTAIN) model for analyzing electronic health records (EHR).

DETAILED DESCRIPTION

Figure 4A:
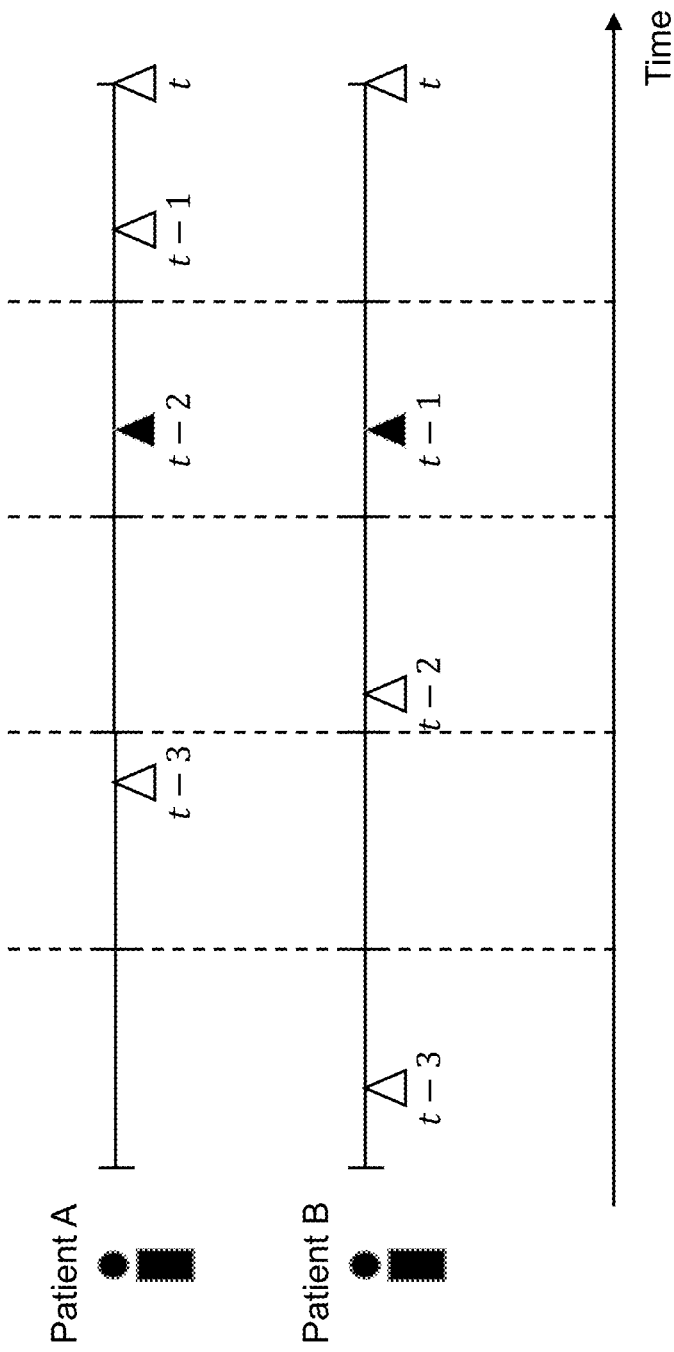
FIG. 4(A) and FIG. 4(B) illustrate an issue of a time step lag in analyzing electronic health records (EHR) of two patients.

Embodiments of the present invention disclose a time-window based attention long short-term memory (TW-LSTM) network. TW-LSTM handles a time step lag between patients by equalizing the time steps of cell states on the basis of the elapsed time until the current time over the patient records. TW-LSTM aligns time steps with each patient on a unified time scale. Thus, TW-LSTM prevents degradation in prediction performance caused by the time step lag and improves the interpretability of the prediction results. Especially, regarding interpretability, TW-LSTM identifies which time is important for the predicted risk because TW-LSTM generates attention weights based on not just the time step but also the elapsed time.

As a previous model, long short-term memory (LSTM), which is a variant of recurrent neural networks (RNN), is used for learning patterns from sequential data. FIG. 1(A) and FIG. 1(B) illustrate a LSTM model used for analyzing electronic health records (EHR). With LSTM, it is assumed that the time intervals between inputs in a sequence are equal, so that LSTM cannot handle the irregular time interval. For example, FIG. 1(A) illustrates visits of a patient (patient A) to medical services. In FIG. 1(A), the horizontal axis is time. FIG. 1(A) shows that patient A has visits at time t, t-1, t-2, and t-3. FIG. 1(B) illustrates LSTM for analyzing EHR corresponding to the patient's visits shown in FIG. 1(A). $x^t$ is an input variable to LSTM at time t, $x^{t-1}$ is an input variable to LSTM at time t-1, $x^{t-2}$ is an input variable to LSTM at time t-2, and $x^{t-3}$ is an input variable to LSTM at time t-3. For the inputs with irregularly spaced elapsed time, LSTM only handles the inputs but ignores the elapsed time intervals.

As another previous method, time-aware long short-term memory (T-LSTM) considers the elapsed time intervals in EHR. FIG. 2(A) and FIG. 2(B) illustrate a T-LSTM model used for analyzing electronic health records (EHR). For example, FIG. 2(A) illustrates visits of a patient (patient A) to medical services at time t, t-1, t-2, and t-3, and also illustrates elapsed time intervals: $\Delta_t$ (an interval between t and t-1), $\Delta_{t-1}$ (an interval between t-1 and t-2), and $\Delta_{t-2}$ (an interval between t-2 and t-3). FIG. 2(B) illustrates T-LSTM for analyzing EHR corresponding to the patient's visits shown in FIG. 2(A). $x^t$ is an input variable to LSTM at time t, $x^{t-1}$ is an input variable to LSTM at time t-1, $x^{t-2}$ is an input variable to LSTM at time t-2, and $x^{t-3}$ is an input variable to LSTM at time t-3. With T-LSTM, when a current cell state of LSTM is updated, a previous cell state is adjusted by a decay function $g(\cdot)$ that depends on the elapsed time. T-LSTM adjusts the previous cell state when updating the current state. By adjusting the previous cell state using the decay function, T-LSTM handles the irregular time intervals. At time t, additional to the input variable $x^t$, $g(\Delta_t)$ is an input. At time t-1, additional to the input variable $x^{t-1}$, $g(\Delta_{t-1})$ is an input. At time t-2, additional to the input variable $x^{t-2}$, $g(\Delta_{t-2})$ is an input.

As yet another previous method, attention-based time-aware disease progression model (ATTAIN) also consider the elapsed time intervals in EHR. FIG. 3(A) and FIG. 3(B) illustrate ATTAIN for analyzing electronic health records (EHR). For example, FIG. 3(A) illustrates visits of a patient (patient A) to medical services at time t, t-1, t-2, and t-3, and also illustrates elapsed time intervals: $\Delta_{tt-1}$ (an interval between t and t-1), $\Delta_{tt-2}$ (an interval between t and t-2), and $\Delta_{tt-3}$ (an interval between t and t-3). FIG. 3(B) illustrates ATTAIN for analyzing EHR corresponding to the patient's visits shown in FIG. 3(A). $x^t$ is an input variable to LSTM at time t, $x^{t-1}$ is an input variable to LSTM at time t-1, $x^{t-2}$ is an input variable to LSTM at time t-2, and $x^{t-3}$ is an input variable to LSTM at time t-3. When a current cell state of LSTM is updated, ATTAIN uses not only just one previous cell state but also a number of previous cell states, and ATTAIN adjusts weights for respective ones of the previous cell states. When a current cell state is updated, respective previous cell states are adjusted by a decay function and aggregated with attention weights.

Figure 4B:
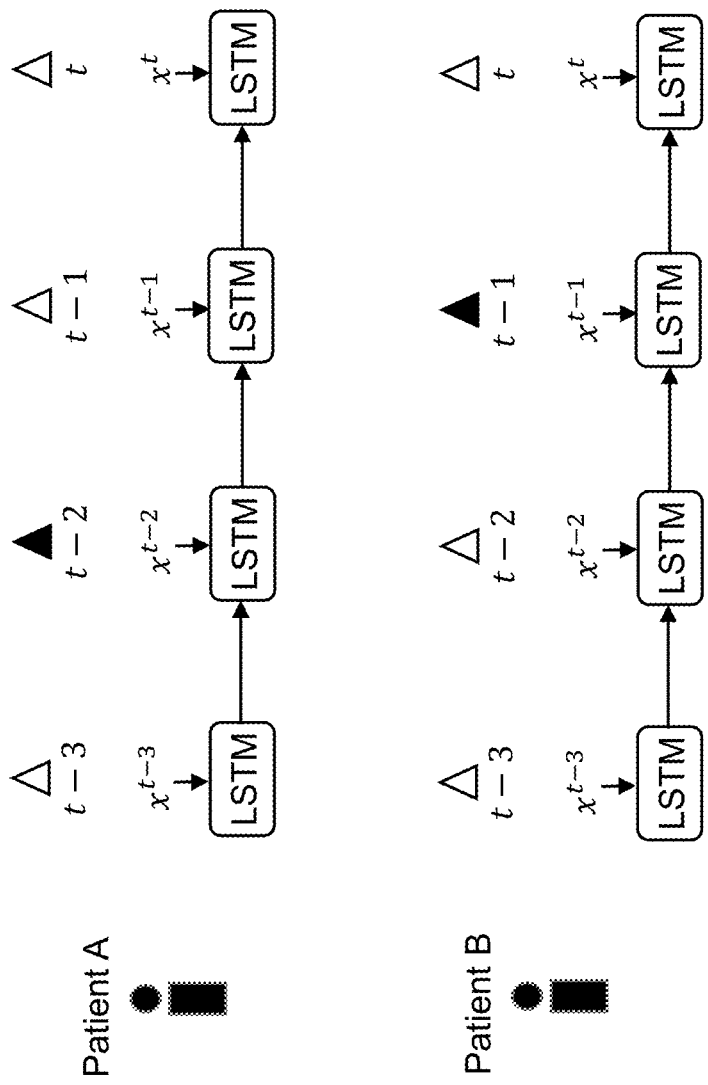

FIG. 4(A) and FIG. 4(B) illustrate an issue of a time step lag in analyzing electronic health records (EHR) of two patients (patient A and patient B). For example, FIG. 4(A) illustrates visits of two patients (patient A and patient B) to medical services at time t, t-1, t-2, and t-3. As shown in FIG. 4(A), although the time interval between the visit at time t-2 and the visit at time t of patient A is equal to the time interval between the visit at time t-1 and the visit at time t of patient B, the numbers of visits are different. For patient A, there are three visits in the time period from t-2 to t; however, for patient B, there are two visits in the time period from t-1 to t. FIG. 4(B) illustrates LSTM, T-LSTM, or ATTAIN for analyzing EHR corresponding to the visits of patient A and patient B shown in FIG. 4(A). Because relationships between the actual elapsed time and the number of visits differ between patient A and patient B, the decay function used in the previous models cannot deal with the difference between the elapsed time and the number of visits. In analyzing EHR of patient A and patient B, it is impossible for the previous models to identify objects with different numbers of observations or the time step.

Figure 5B:
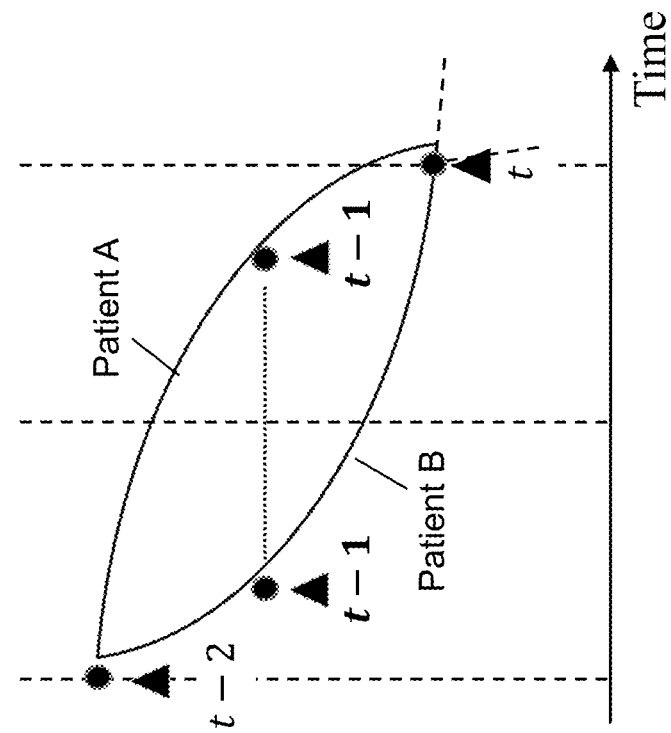
FIG. 5(A) and FIG. 5(B) illustrate another issue of a time step lag in analyzing electronic health records (EHR) of two patients.
Figure 5A:
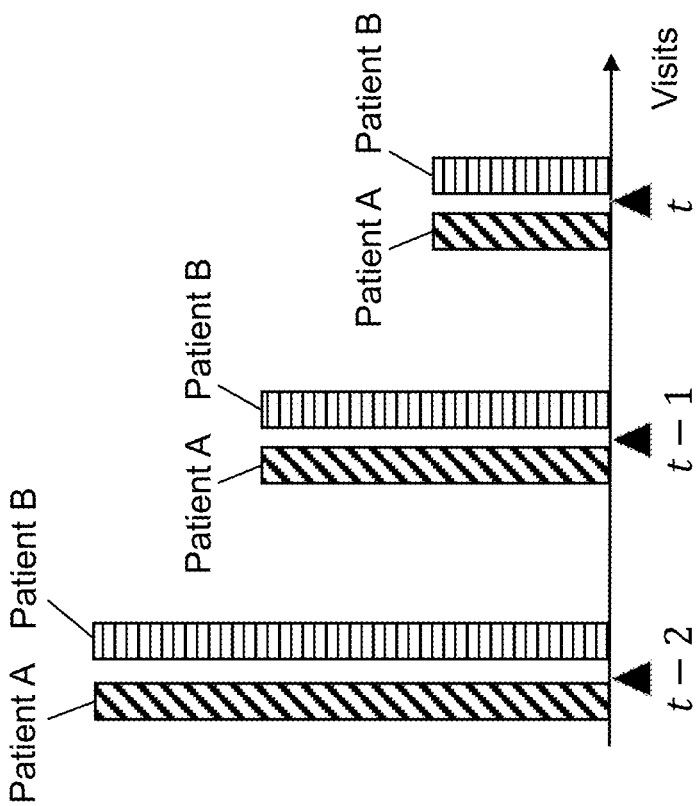

FIG. 5(A) and FIG. 5(B) illustrate another issue of a time step lag in analyzing electronic health records (EHR) of two patients. In FIG. 5(A), the horizontal axis represents time of visits of patient A and patient B, showing visits of patient A and patient B at t, t-1, t-2; the bars represent values of attention weights in ATTAIN. In FIG. 5(B), curves represent values of lab tests. As shown in FIG. 5(A) and FIG. 5(B), although time variations are different because of the time step lag between patient A and patient B, the same attention weights are generated if only values without the elapsed time are considered. Because the attention mechanism in ATTAIN cannot capture such time variations with fluctuating observation intervals, it is essential to deal with the time step lag in order to improve prediction performance and interpretability.

In this document, the boldfaced variables are vectors. It is assumed that each record of a single patient is represented as a sequence of patient information at visits, $X=\{x^1, \ldots, x^t\}$, where its k-th element is a D-dimensional feature vector, $x^k \in \mathbb{R}^D$, the superscripts of x are the time steps of visits, and t is the total number of visits. The target variable y is a binary variable (0/1), where 1 refers to an occurrence of an event and 0 represents no occurrence. The goal is to predict y from X.

Before TW-LSTM of the present invention is described in detail in next paragraphs, the standard LSTM is described as follows. LSTM is an RNN variant designed to capture long-term dependencies. The standard LSTM for the t-th observation $x^t$ is defined as:

$$i^t = \sigma(W_i x^t + U_i h^{t-1} + b_i) \quad (1)$$

$$f^t = \sigma(W_f x^t + U_f h^{t-1} + b_f) \quad (2)$$

$$c^t = f^t \circ c^{t-1} + i^t \circ \tanh(W_c x^t + U_c h^{t-1} + b_c) \quad (3)$$

$$o^t = \sigma(W_o x^t + U_o h^{t-1} + b_o) \quad (4)$$

$$h^t = o^t \circ \tanh(c^t) \quad (5)$$

where $i^t$, $f^t$, and $o^t$ are the input gate, the forget gate, and the output gate, respectively, where $h^{t-1}$ and $h^t$ are the previous and current hidden states, where $c^{t-1}$ and $c^t$ are the previous and current cell states, where $\sigma$ is the sigmoid function, where the operator denotes the element-wise product, where $W_i, W_f, W_c, W_o \in \mathbb{R}^{H \times D}$, $U_i, U_f, U_c, U_o \in \mathbb{R}^{H \times D}$, and $b_i, b_f, b_c, b_o \in \mathbb{R}^{H \times D}$ are the network parameters, and where H is the number of units of the hidden nodes.

Figure 6:
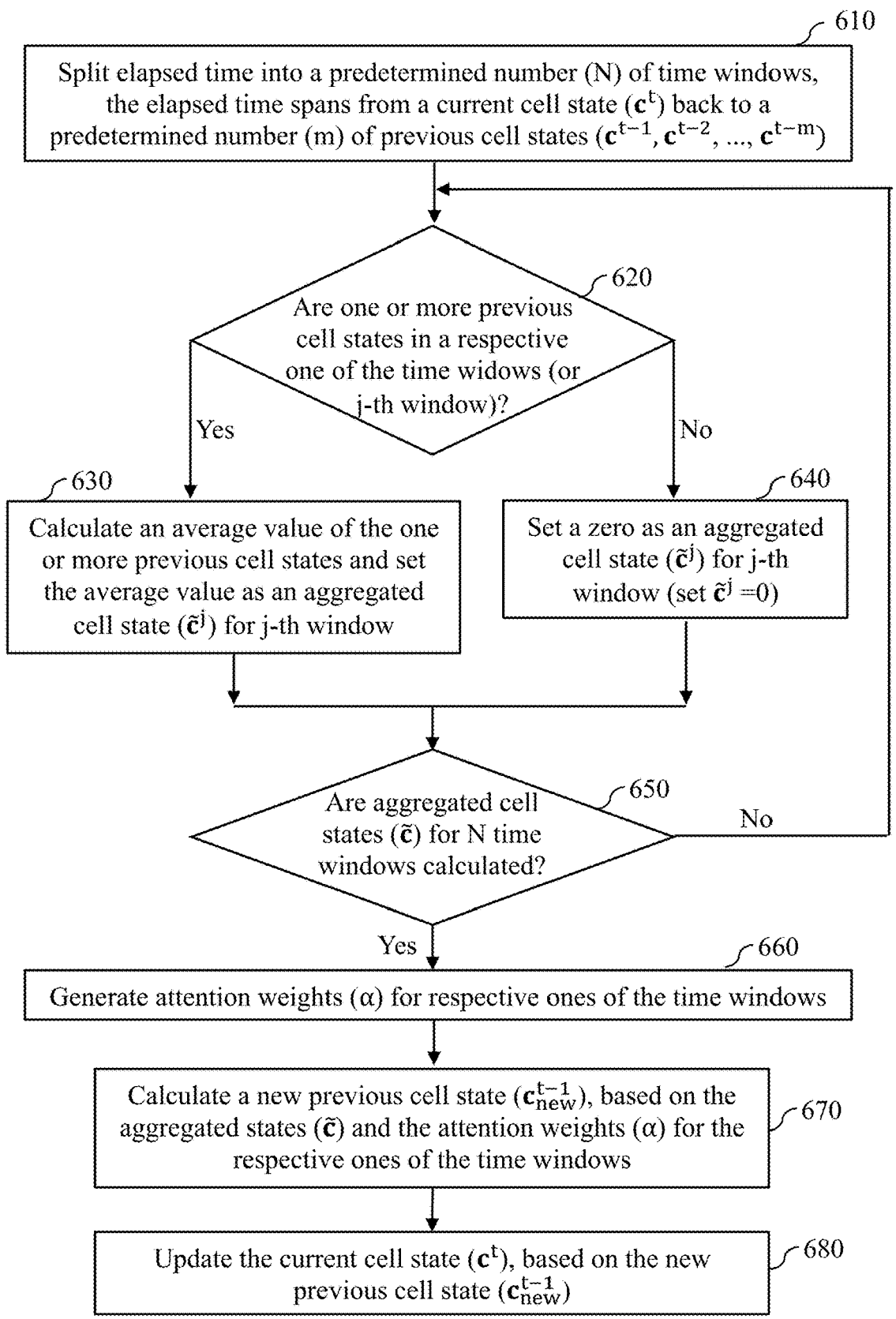
FIG. 6 presents a flowchart showing operational steps of using a time-window based attention long short-term memory (TW-LSTM) network to analyze sequential data with time irregularity, in accordance with one embodiment of the present invention.

FIG. 6 presents a flowchart showing operational steps of using a time-window based attention long short-term memory (TW-LSTM) network to analyze sequential data with time irregularity, in accordance with one embodiment of the present invention. The operation steps are implemented on one or more computing devices or servers. A computing device or server is described in more detail in later paragraphs with reference to FIG. 9. In another embodiment, the operational steps may be implemented on a virtual machine or another virtualization implementation being run on one or more computing devices or servers. In yet another embodiment, the operational steps may be implemented in a cloud computing environment. The cloud computing environment is described in later paragraphs with reference to FIG. 10 and FIG. 11.

Figure 7:
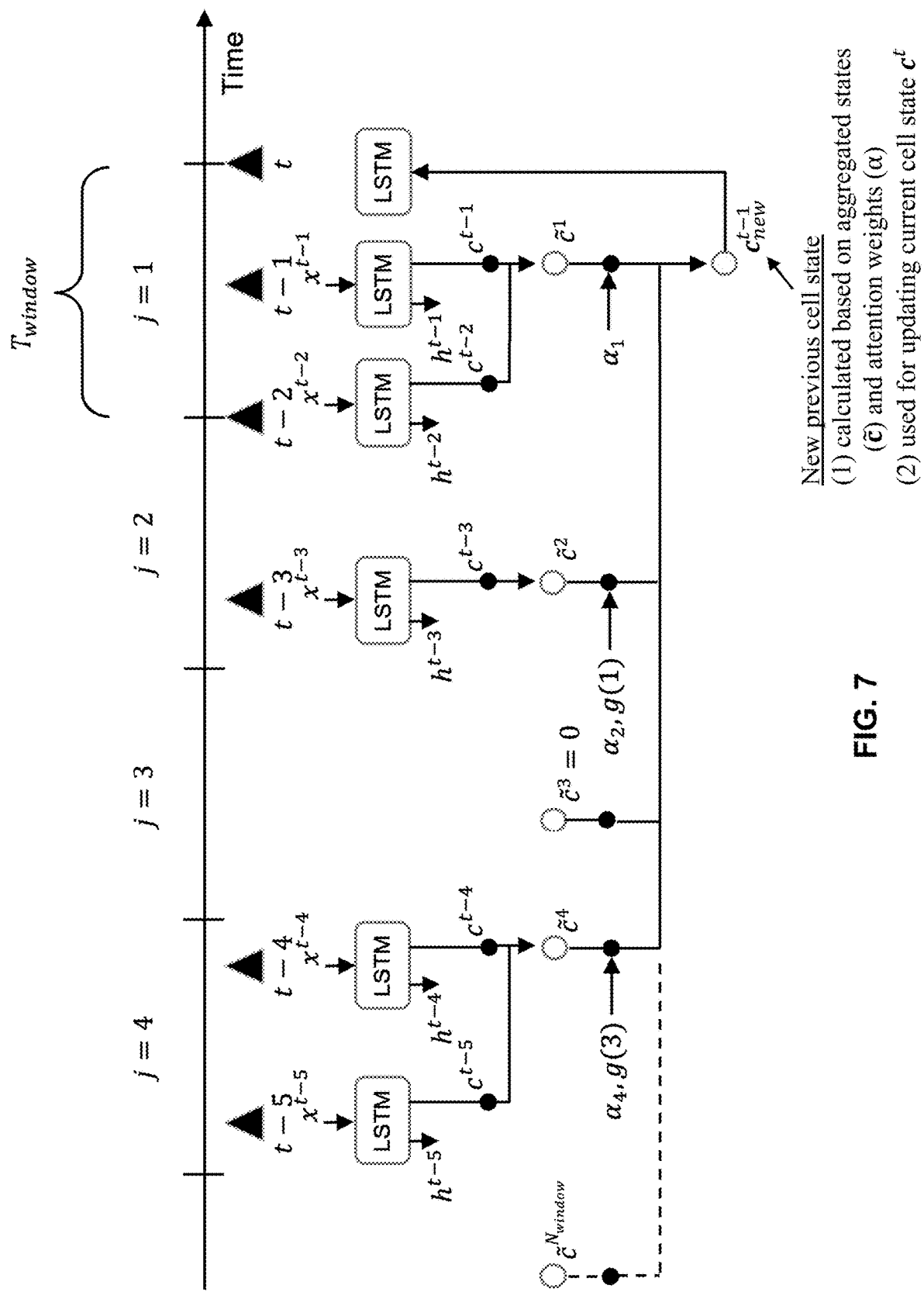
FIG. 7 illustrates a time-window based attention long short-term memory (TW-LSTM) network, in accordance with one embodiment of the present invention.

At step 610, the computing device or server splits elapsed time into a predetermined number (N) of time windows. In the elapsed time, there are a predetermined number (m) of previous cell states ($c^{t-1}, c^{t-2}, \ldots, c^{t-m}$). m is a hyperparameter. In the example shown in FIG. 7, m=5. The elapsed time spans from the time of a current cell state ($c^t$) back to the time of m-th previous cell state (or earliest previous cell state). The elapsed time is split with a constant time interval $T_{window}$ which is a hyperparameter. FIG. 7 shows the constant time interval $T_{window}$ and the time windows. In the example shown in FIG. 7, the elapsed time is split into four time windows (N=4).

At step 620, the computing device or server determines whether one or more previous cell states are in a respective one of the time windows (or j-th time window). For example, shown in FIG. 7, in the time window of j=1, there are two previous cell states $c^{t-1}$ and $c^{t-2}$; in the time window of j=2, there is one previous cell state $c^{t-3}$; in the time window of j=3, there is no previous cell state; and in the time window of j=4, there are two previous cell states $c^{t-4}$ and $c^{t-5}$.

In response to determining that the one or more previous cell states are in the respective one of the time windows or j-th time window ("Yes" branch of decision step 620), at step 630, the computing device or server calculates an average value of the one or more previous cell states in j-th time window and set the average value as an aggregated cell state ($\tilde{c}^j$) for j-th time window. In response to determining that the one or more previous cell states are not in the respective one of the time windows or j-th time window ("No" branch of decision step 620), at step 640, the computing device or server sets a zero as the aggregated cell state ($\tilde{c}^j$) for time window j (i.e., the computing device or server sets $\tilde{c}^j=0$). The aggregated cell state ($\tilde{c}^j$) is designated to j-th time window; in other words, for each time window, there is one aggregated cell state. In the example shown in FIG. 7, in the time window of j=1, the computing device or server calculates an average of two previous cell states $c^{t-1}$ and $c^{t-2}$ and set the average value of $c^{t-1}$ and $c^{t-2}$ as $\tilde{c}^1$. In the time window of j=2, since the time window of j=2 has only one previous cell state $c^{t-3}$, the average value is equal to $c^{t-3}$; the computing device or server sets the value of $c^{t-3}$ as $\tilde{c}^2$. In the time window of j=3, since there is no previous cell state, the commuting device or server sets $\tilde{c}^3=0$. In the time window of j=4, the computing device or server calculates an average of two previous cell states $c^{t-4}$ and $c^{t-5}$ and set the average value of $c^{t-4}$ and $c^{t-5}$ as $\tilde{c}^4$.

The aggregated cell state ($\tilde{c}^j$) in j-th time window is calculated as follows:

$$\tilde{c}^j = \frac{1}{M_j} \sum_{i=t-m}^{t-1} c^i g(j-1) \chi(j, \Delta t_{ti}) \quad (\text{for } j=1, \ldots, N) \quad (6)$$

$$M_j = \sum_{i=t-m}^{t-1} \chi(j, \Delta t_{ti}) \quad (\text{for } j=1, \ldots, N) \quad (7)$$

$$\chi(j, \Delta t_{ti}) = \begin{cases} 1, & (j-1)T_{window} \leq \Delta t_{ti} < jT_{window} \\ 0, & \text{otherwise} \end{cases} \quad (8)$$

where $c^i$ is a cell state and calculated by using equation (3), $g(\cdot)$ is a decay function, $\chi$ is a masking function which only select relevant cell states belonging to the time window index j, N is a hyperparameter representing the total number of time windows (e.g., N=4 in the example shown in FIG. 7), and $\Delta t_{ti}$ is the time interval between the i-th observation to the current t-th observation. $\tilde{c}^j$, $M_j$, and $\chi(j, \Delta t_{ti})$ are defined for j-th time window, and they are specific for each time window. $c^i$ and $\Delta t_{ti}$ are defined are defined for input variable $x^i$.

Referring to FIG. 6, at step 650, the computing device or server determines whether aggregated cell states ($\tilde{c}$) are calculated for N time windows. In response to determining that the aggregated cell states ($\tilde{c}$) are not calculated for all the N time windows ("No" branch of decision block 650), the computing device or server reiterates steps 620, 630 or 640, and 650, until the aggregated cell states are calculated for all the N time windows.

In response to determining that the aggregated cell states ($\tilde{c}$) are calculated for all the N time windows ("Yes" branch of decision block 650), at step 660, the computing device or server generates attention weights ($\alpha$) for respective ones of the time windows. In the example shown in FIG. 7, an attention weight $\alpha_1$ is determined for the time window of j=1, an attention weight $\alpha_2$ is determined for the time window of j=2, and an attention weight $\alpha_4$ is determined for the time window of j=4.

The attention weights are determined as follows:

$$e_j = W_a \tilde{c}^j \text{ (for } j=1, \ldots, N) \tag{6}$$

where $W_a \in \mathbb{R}^{1 \times H}$ is a network parameter. Thus, $e_1$, $e_2, \ldots, e_N$ are obtained for N time windows, respectively. Then, the softmax function is used to generate the attention weights as follows:

$$\alpha_1, \alpha_2, \ldots, \alpha_N = \text{softmax}(e_1, e_2, \ldots e_N) \tag{7}$$

In the case that $e_j=0$, the computing device or server replaces $e_j$ with a small negative value (e.g., $-10^{-7}$) so that the attention weights can be properly calculated by the softmax function.

In ATTAIN, the attention weights are generated from the original inputs x. Because ATTAIN captures the observation defined by just x, it cannot capture time variations in consideration of the elapsed time. In contrary, TW-LSTM in the present invention uses cell states to generate the attention weights.

Referring to FIG. 6, at step 670, the computing device or server calculates a new previous cell state ($c_{new}^{t-1}$), based on the aggregated cell states ($\tilde{c}$) and the attention weights ($\alpha$). The aggregated cell states ($\tilde{c}$) are determined through steps 620, 630 or 640, and 650; the attention weights (a) are determined at step 660. The new previous cell state ($c_{new}^{t-1}$) is calculated as follows:

$$c_{new}^{t-1} = \sum_{j=1}^{N} \alpha_j \tilde{c}^j \tag{8}$$

At step 670, the computing device or server updates the current cell state ($c^t$), based on the new previous cell state ($c_{new}^{t-1}$). When updating the current cell state ($c^t$) by using equations (1)-(5), the computing device or server replaces the previous cell state ($c^{t-1}$, which is a previous cell state immediate before the current cell state) with the new previous cell state ($c_{new}^{t-1}$). The updated current cell state is calculated from the new previous cell state ($c_{new}^{t-1}$), a previous hidden state ($h^{t-1}$), and a current input ($x^t$).

The computing device or server predicts the true label y as follows:

$$\hat{y} = \sigma(W_p h^t + b_p) \tag{9}$$

where $W_p \in \mathbb{R}^{1 \times H}$ and $b_p \in \mathbb{R}^1$ are network parameters. The prediction of y is based on a current hidden state ($h^t$) that is generated from the updated current cell state ($c^t$). Furthermore, cross entropy is used as the objective function as follows:

$$l(\hat{y}, y) = \sum_{l=1}^{n} [y_1 \ln \hat{y}_1 + (1 - y_1) \ln(1 - y_1)] \tag{10}$$

where $\hat{y}_1$ and $y_1$ are values of the prediction and true labels of each record for 1-th sample of a mini-batch, respectively. The upper limit of summation n is a mini-batch size.

Figure 8:
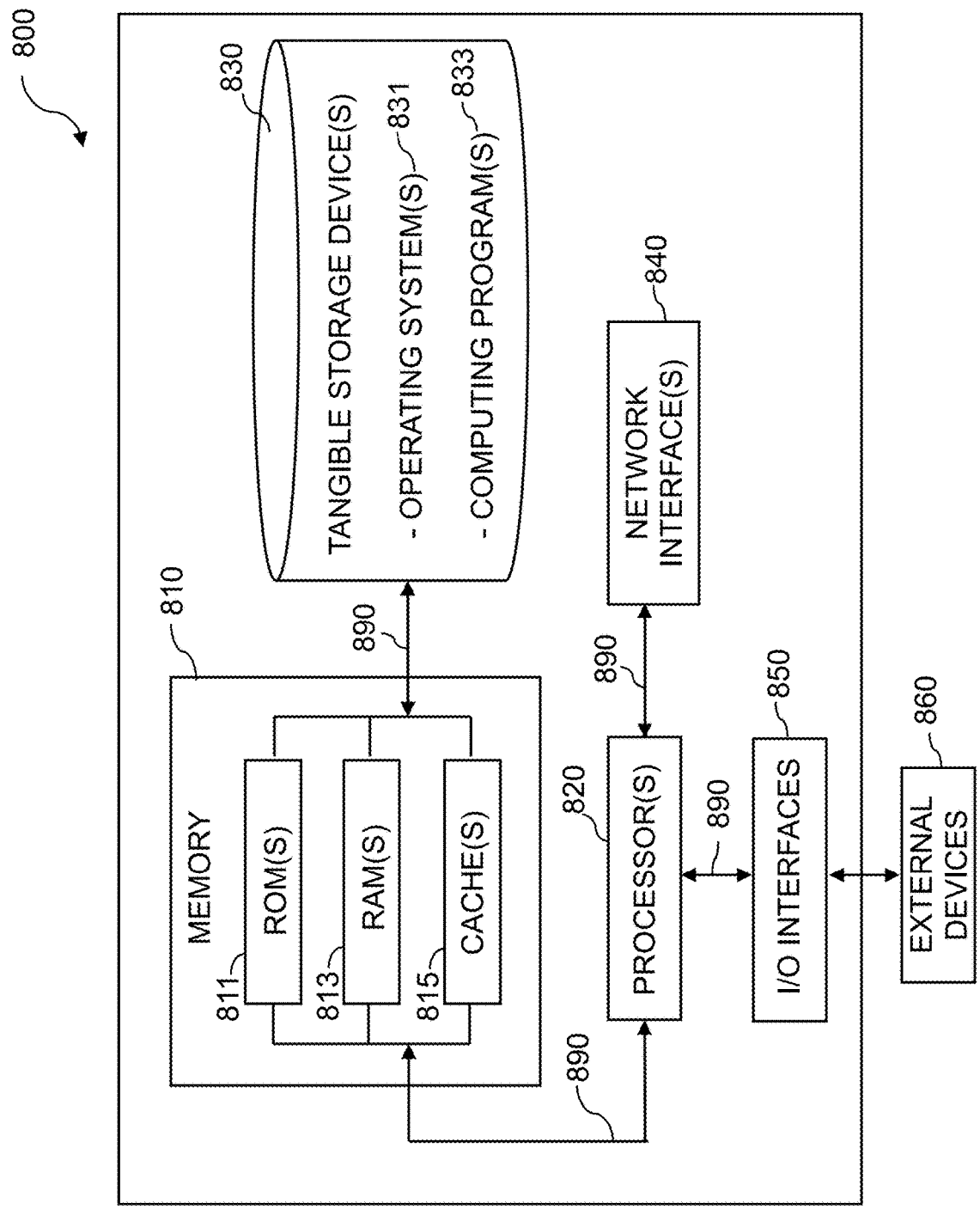
FIG. 8 is a diagram illustrating components of a computing device or server, in accordance with one embodiment of the present invention.

FIG. 8 is a diagram illustrating components of computing device or server 800, in accordance with one embodiment of the present invention. It should be appreciated that FIG. 8 provides only an illustration of one implementation and does not imply any limitations with regard to the environment in which different embodiments may be implemented.

Referring to FIG. 8, computing device or server 800 includes processor(s) 820, memory 810, and tangible storage device(s) 830. In FIG. 8, communications among the above-mentioned components of computing device or server 800 are denoted by numeral 890. Memory 810 includes ROM(s) (Read Only Memory) 811, RAM(s) (Random Access Memory) 813, and cache(s) 815. One or more operating systems 831 and one or more computer programs 833 reside on one or more computer readable tangible storage device(s) 830.

Computing device or server 800 further includes I/O interface(s) 850. I/O interface(s) 850 allows for input and output of data with external device(s) 860 that may be connected to computing device or server 800. Computing device or server 800 further includes network interface(s) 840 for communications between computing device or server 800 and a computer network.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the C programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 9:
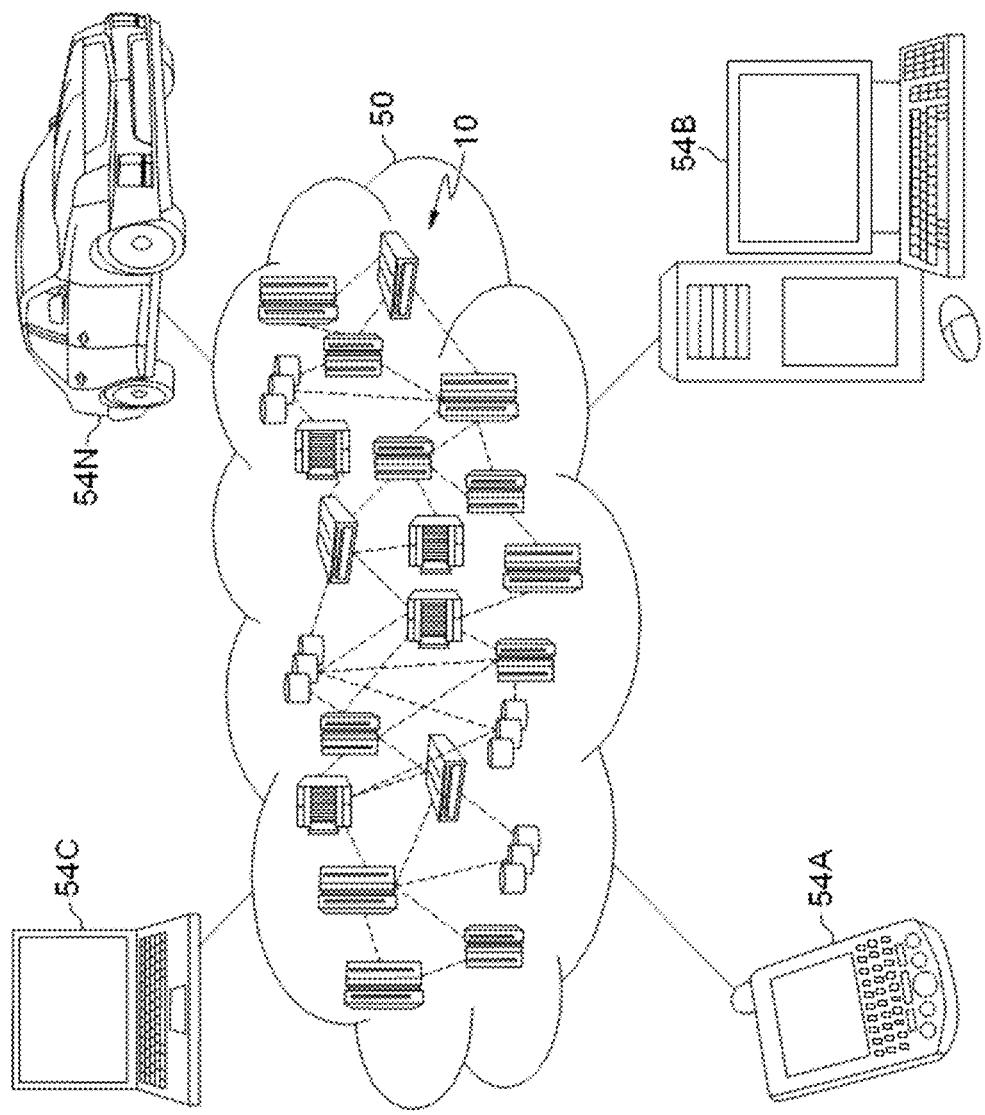
FIG. 9 depicts a cloud computing environment, in accordance with one embodiment of the present invention.

Referring now to FIG. 9, illustrative cloud computing environment 50 is depicted. As shown, cloud computing environment 50 includes one or more cloud computing nodes 10 with which local computing devices are used by cloud consumers, such as mobile device 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N are intended to be illustrative only and that computing nodes 10 and cloud computing environment 50 can communicate with any type of computerized device over any type of network and/or network addressable connection (e.g., using a web browser).

Figure 10:
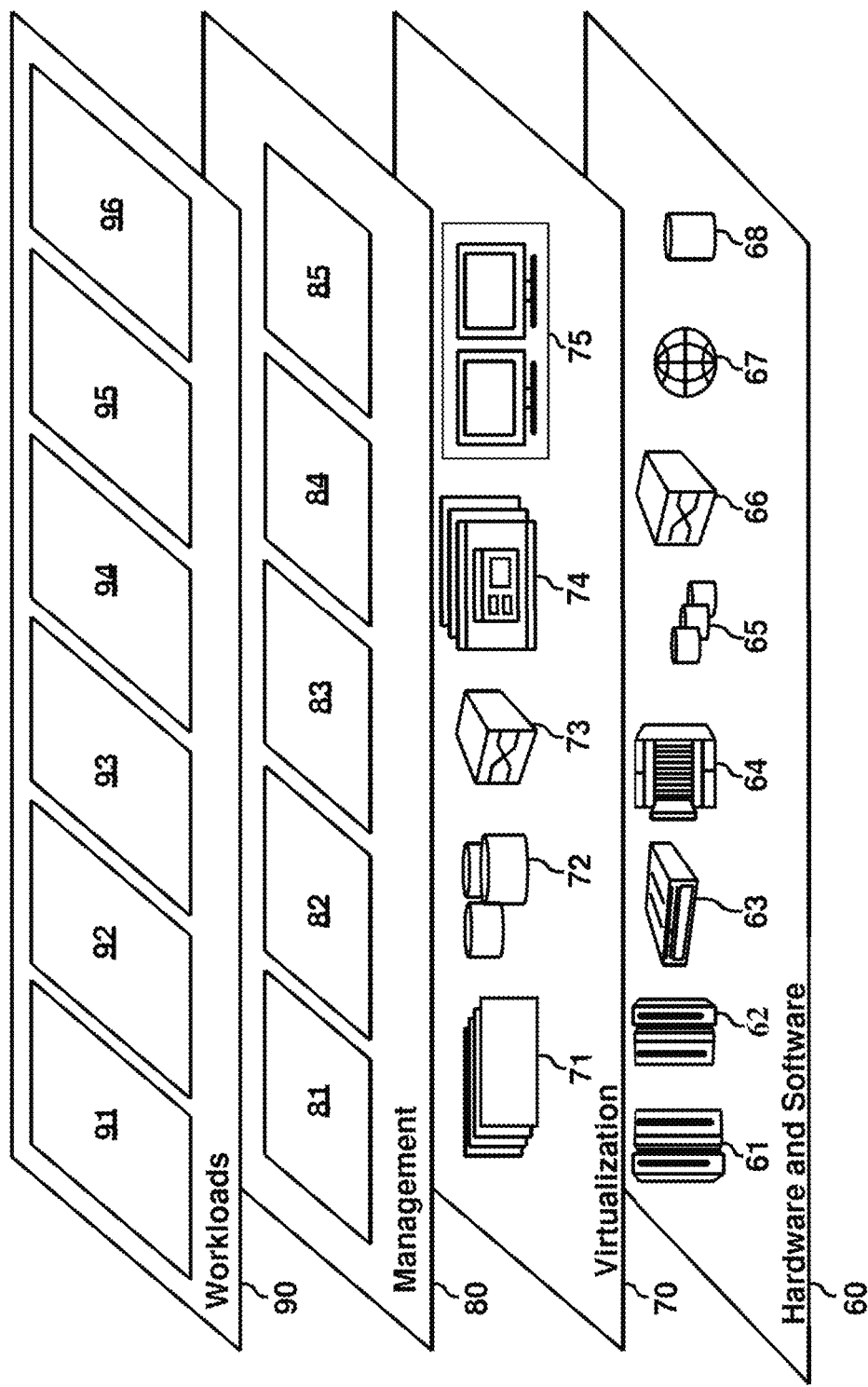
FIG. 10 depicts abstraction model layers in a cloud computing environment, in accordance with one embodiment of the present invention.

Referring now to FIG. 10, a set of functional abstraction layers provided by cloud computing environment 50 (FIG. 9) is shown. It should be understood in advance that the components, layers, and functions shown in FIG. 10 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and function 96. Function 96 is the functionality of using the TW-LSTM network to analyze sequential data with time irregularity.

What is claimed is:

1. A computer-implemented method for a time-window based attention long short-term memory network (TW-LSTM network), the method comprising:
   a time-window based attention long short-term memory network (TW-LSTM network) splitting elapsed time into a predetermined number of time windows, wherein the elapsed time spans from a current cell state back to a predetermined number of previous cell states, wherein respective ones of the windows have respective numbers of cell states;
   the TW-LSTM network calculating average values of the previous cell states in the respective ones of the time windows;
   the TW-LSTM network setting the average values as aggregated cell states for the respective ones of the time windows;

the TW-LSTM network generating attention weights for the respective ones of the time windows;

the TW-LSTM network calculating a new previous cell state, based on the aggregated cell states and the attention weights, wherein the new previous cell state is a weighted summation of the aggregated cell states;

the TW-LSTM network updating the current cell state, based on the new previous cell state; and the TW-LSTM network predicting a target variable for sequential data with time irregularity, based on a current hidden state that is generated from an updated current cell state.

2. The computer-implemented method of claim 1, further comprising:

the TW-LSTM network determining whether the previous cell states are in a respective one of the time windows;

in response to determining that the previous cell states are in the respective one of the time windows, the TW-LSTM network calculating an average of the previous cell states in the respective one of the time windows and setting the average as an aggregated cell state for the respective one of the time windows; and in response to determining that the previous cell states are not in the respective one of the time windows, the TW-LSTM network setting a zero as the aggregated cell state.

3. The computer-implemented method of claim 1, wherein the elapsed time is split with a constant time interval, wherein the constant time interval is a hyperparameter.

4. The computer-implemented method of claim 1, wherein, in the elapsed time, there are a predetermined number of the previous cell states, the predetermined number of the previous cell states is a hyperparameter.

5. The computer-implemented method of claim 1, wherein the attention weights are generated based on respective ones of the aggregated cell states and a TW-LSTM network parameter.

6. The computer-implemented method of claim 1, wherein, in calculation for updating the current cell state, a previous cell state that is immediately before the current cell state is replaced with the new previous cell state.

7. A computer program product for a time-window based attention long short-term memory network (TW-LSTM network), the computer program product comprising a computer readable storage medium having program instructions of the TW-LSTM network embodied therewith, the program instructions of the TW-LSTM network executable by one or more processors, the program instructions of the TW-LSTM network executable to:

split elapsed time into a predetermined number of time windows, wherein the elapsed time spans from a current cell state back to a predetermined number of previous cell states, wherein respective ones of the windows have respective numbers of cell states;

calculate average values of the previous cell states in the respective ones of the time windows;

set the average values as aggregated cell states for the respective ones of the time windows;

generate attention weights for the respective ones of the time windows;

calculate a new previous cell state, based on the aggregated cell states and the attention weights, wherein the new previous cell state is a weighted summation of the aggregated cell states;

update the current cell state, based on the new previous cell state; and predict a target variable for sequential data with time irregularity, based on a current hidden state that is generated from an updated current cell state.

8. The computer program product of claim 7, further comprising the program instructions of the TW-LSTM network executable to:

determine whether the previous cell states are in a respective one of the time windows;

in response to determining that the previous cell states are in the respective one of the time windows, calculate an average of the previous cell states in the respective one of the time windows and setting the average as an aggregated cell state for the respective one of the time windows; and in response to determining that the previous cell states are not in the respective one of the time windows, set a zero as the aggregated cell state.

9. The computer program product of claim 7, wherein the elapsed time is split with a constant time interval, wherein the constant time interval is a hyperparameter.

10. The computer program product of claim 7, wherein, in the elapsed time, there are a predetermined number of the previous cell states, the predetermined number of the previous cell states is a hyperparameter.

11. The computer program product of claim 7, wherein the attention weights are generated based on respective ones of the aggregated cell states and a TW-LSTM network parameter.

12. The computer program product of claim 7, wherein, in calculation for updating the current cell state, a previous cell state that is immediately before the current cell state is replaced with the new previous cell state.

13. A computer system for a time-window based attention long short-term memory network (TW-LSTM network), the computer system comprising:

one or more processors, one or more computer readable tangible storage devices, and the TW-LSTM network stored on at least one of the one or more computer readable tangible storage devices for execution by at least one of the one or more processors;

the TW-LSTM network splitting elapsed time into a predetermined number of time windows, wherein the elapsed time spans from a current cell state back to a predetermined number of previous cell states, wherein respective ones of the windows have respective numbers of cell states;

the TW-LSTM network calculating average values of the previous cell states in the respective ones of the time windows;

the TW-LSTM network setting the average values as aggregated cell states for the respective ones of the time windows;

the TW-LSTM network generating attention weights for the respective ones of the time windows;

the TW-LSTM network calculating a new previous cell state, based on the aggregated cell states and the attention weights, wherein the new previous cell state is a weighted summation of the aggregated cell states;

the TW-LSTM network updating the current cell state, based on the new previous cell state; and the TW-LSTM network predicting a target variable for sequential data with time irregularity, based on a current hidden state that is generated from an updated current cell state.

14. The computer system of claim 13, further comprising:

the TW-LSTM network determining whether the previous cell states are in a respective one of the time windows;

in response to determining that the previous cell states are in the respective one of the time windows, the TW-LSTM network calculating an average of the previous cell states in the respective one of the time windows and setting the average as an aggregated cell state for the respective one of the time windows; and in response to determining that the previous cell states are not in the respective one of the time windows, the TW-LSTM network setting a zero as the aggregated cell state.

15. The computer system of claim 13, wherein the elapsed time is split with a constant time interval, wherein the constant time interval is a hyperparameter.

16. The computer system of claim 13, wherein, in the elapsed time, there are a predetermined number of the previous cell states, the predetermined number of the previous cell states is a hyperparameter.

17. The computer system of claim 13, wherein the attention weights are generated based on respective ones of the aggregated cell states and a TW-LSTM network parameter.

18. The computer system of claim 13, wherein, in calculation for updating the current cell state, a previous cell state that is immediately before the current cell state is replaced with the new previous cell state.

\* \* \* \* \*